(12) United States Patent
Goade et al.

(10) Patent No.: US 6,197,497 B1
(45) Date of Patent: *Mar. 6, 2001

(54) IMMUNOASSAY FOR HERPES SIMPLEX VIRUS

(75) Inventors: Diane E. Goade; Richard Bell; Steven Jenison, all of Albuquerque, NM (US)

(73) Assignee: University of New Mexico, Albuquerque, NM (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/632,537

(22) Filed: Apr. 19, 1996

Related U.S. Application Data

(63) Continuation-in-part of application No. 08/426,604, filed on Apr. 21, 1995, now abandoned.

(51) Int. Cl.$^7$ ...................................................... C12Q 1/70
(52) U.S. Cl. ............................................... 435/5; 530/324
(58) Field of Search .................................. 435/5; 530/324, 530/350

(56) References Cited

U.S. PATENT DOCUMENTS 4,642,333   2/1987   Person .
5,244,792 * 9/1993   Burke et al. ........................ 435/69.3

FOREIGN PATENT DOCUMENTS 0175787   4/1997   (EP) .

OTHER PUBLICATIONS

Burke, R.L., "Contemporary Approaches to Vaccination Against Herpes Simplex Virus," *curr. Topics. Microbiol. Immunol.*, vol. 179, pp 137–158 (1992).

Mester, J.C., et al., "Herpes Simplex Virus Type 1—Specific Immunity Induced by peptides Corresponding to an Antigenic site of Glycoprotein B," *J of Virology*, pp 4277–5283 (Nov. 1990).

Burke, Rae Lyn, Development of a Herpes Simplex Virus Subunit Glycoprotein Vaccine for Prophylactic and Therapeutic Use, *Reviews of Infectious Diseases* 13(Suppl 11:S906–11 (1991).

Eberle, R. et al., Topological Distribution of Virus–Specific and Cross–Reactive Antigenic Determinants on the gB Glycoprotein of the Herpes Simplex Viruses, *Journal of Medical Virology* 27:309–316 (1989).

Pereira, Lenore et al., Domain Structure of Herpes Simplex Virus 1 Glycorpotein B: Neutralizing Epitopes Map in Regions of continuous and Discontinuous Residues, *Virology* 172:11–24 (1989) AT.

Qadri, Concepcion Gimeno et al., Mutations in Conformation–Dependent Domains of Herpes Simplex Virus 1 Glycoprotein B Affect the antigenic Properties, Dimerization, and Transport of the Molecule, *Virology* 180, 1991,135–152.

Stanberry, Lawrence R, Herpes Simplex Virus Vaccines, *Seminars in Pediatric Infectious Diseases*, vol. 1, No. 3 (Jul.) 1991: pp. 178–185.

Van Regenmortel, M.H.V., Herpes Simplex Virus, Immunochemistry of Viruses II, The Basis for Serodiagnosis and Vaccines, 1990, pp. 459–481.

Wong, K.K., Jr. et al., Controlling Herpes Simplex Virus Infections: Is Intracellualr Immunization the Way of the Future? *Microbiology and Immunology*, vol. 179, pp. 159–174, 1992.

Goade, D.E., et al., Mapping of HSV–2 Glycoprotein B Regions That React with Human Antibodies:Identification of Discrete Type–specific and Type–common Regions, (Abstract), International Herpes Virus Meetings, (Netherlands) Jul. 1995.

ISAR Conference, Apr. 1995 (Abstract), HSV–2 glycoprotein B has previously been shown to include an epitope . . . .

Goade, D., et al., Epitopes of Herpes Simplex Virus Type 2 Glycoprotein B That are Recognized by Human Antibodies: Type Specific and Cross Reactive Regions, ICAAC Abstract, Orlando, FL, Oct. 4–7, 1994.

Webster's New Riverside University Dictionary, The Riverside Publishing Company, Boston, p. 1156, 1994.*

Sanchez–Pescador et al., "Antibodies to epitopes of herpes simplex virus type 1 glycoprotein b (gB) in human sera: analysis of functional gB epitopes defined by inhibition of murine monoclonal antibodies", The Journal Of Infectious Diseases, 168:844–53, 1993.*

* cited by examiner

*Primary Examiner*—Donna C. Wortman
*Assistant Examiner*—Brenda G. Brumback
(74) *Attorney, Agent, or Firm*—Stephen A. Slusher; Nancy E. Ownbey; Jefrey D. Myers

(57) ABSTRACT

The invention provides segments of HSV-1 and HSV-2 glycoprotein B which include antigenic epitopes in the gB amino-proximal region that react with human antibodies in a type-specific manner, and epitopes in the gB carboxy-proximal region that cross-react with HSV-1 and HSV-2 antibodies.

16 Claims, 10 Drawing Sheets

Figure 1:
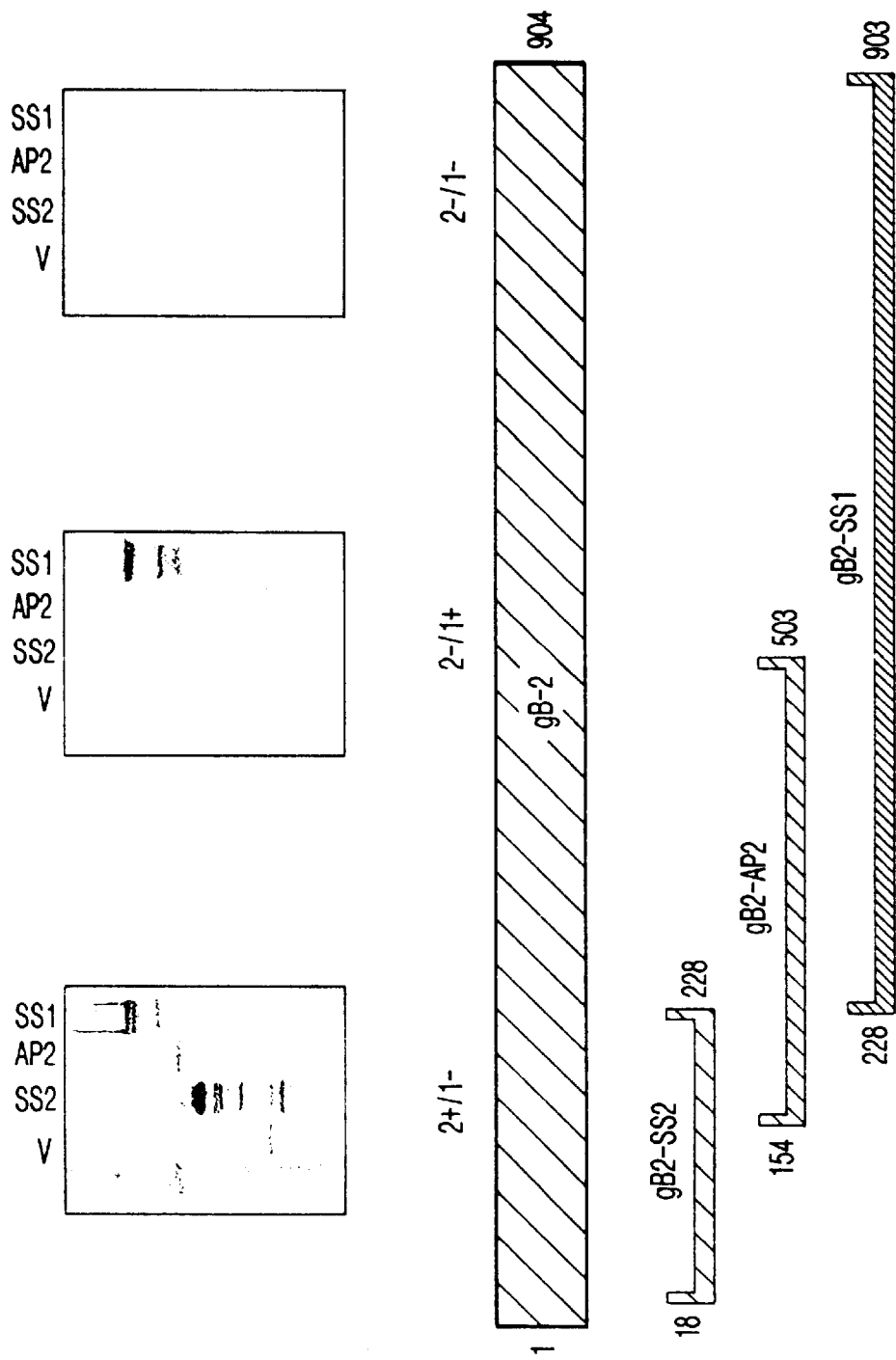
Figure 2:
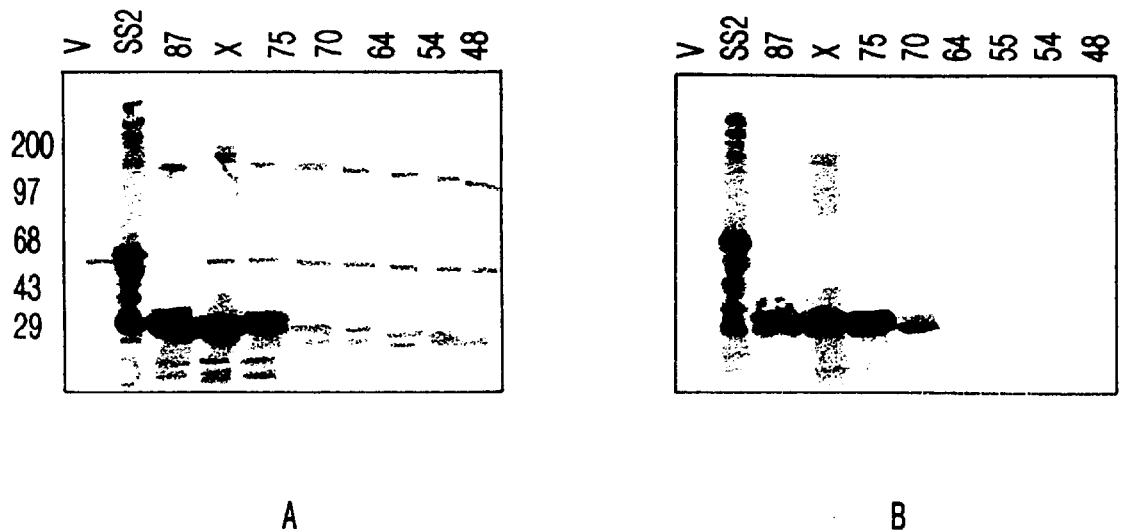
Figure 6:
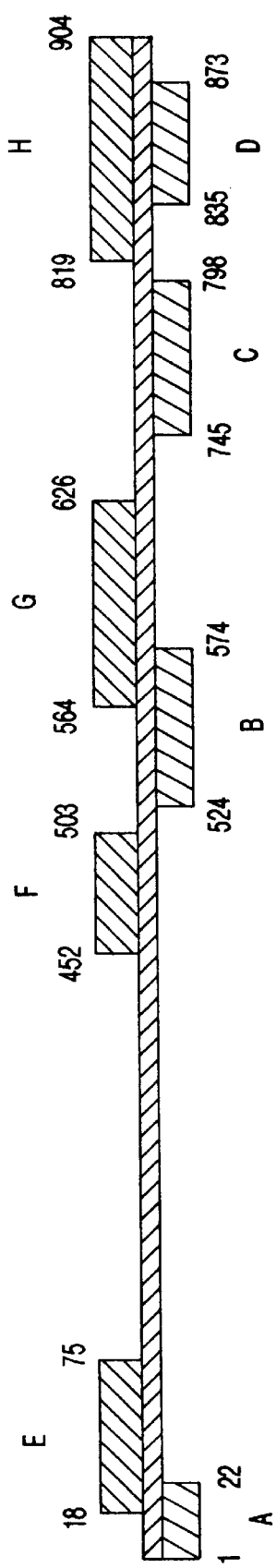

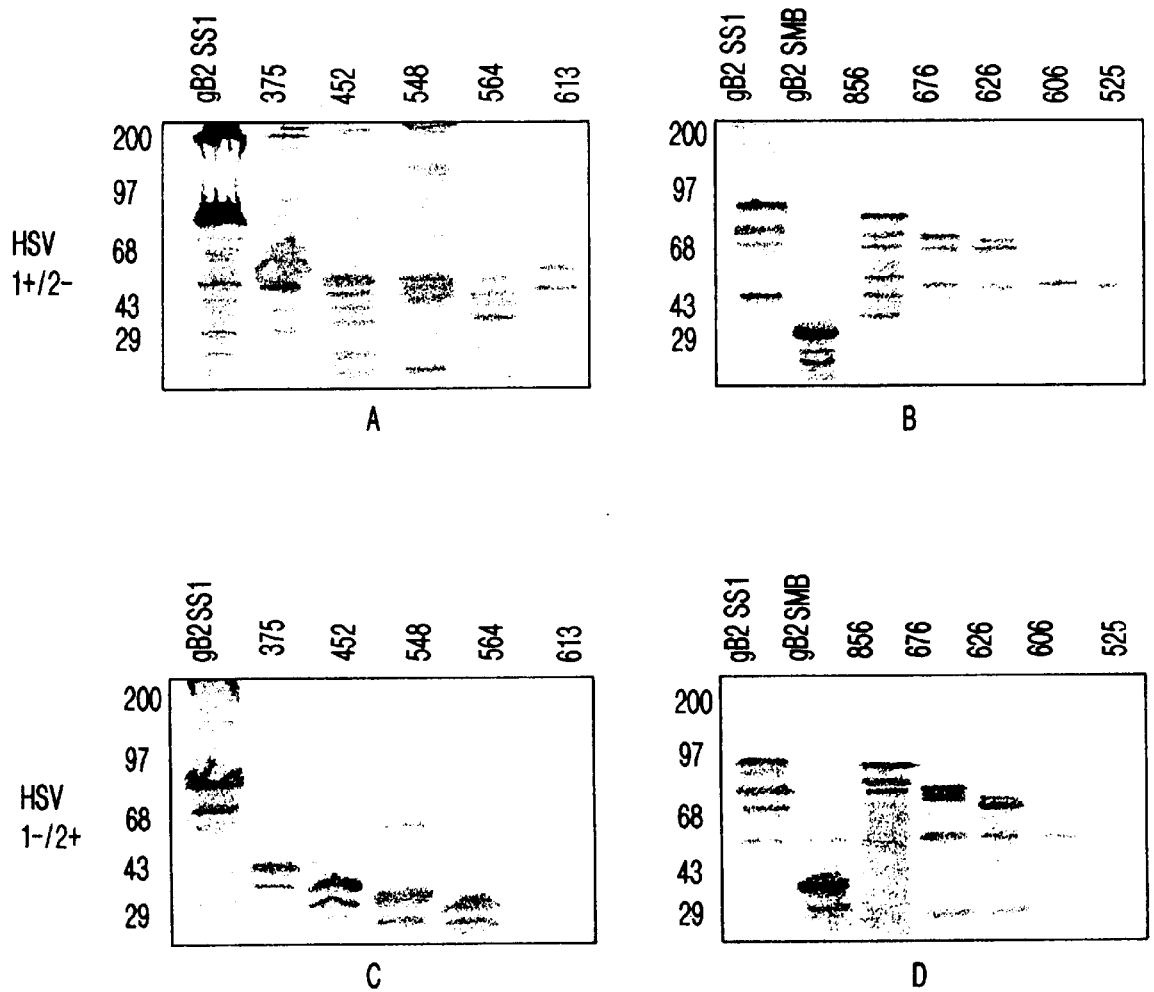
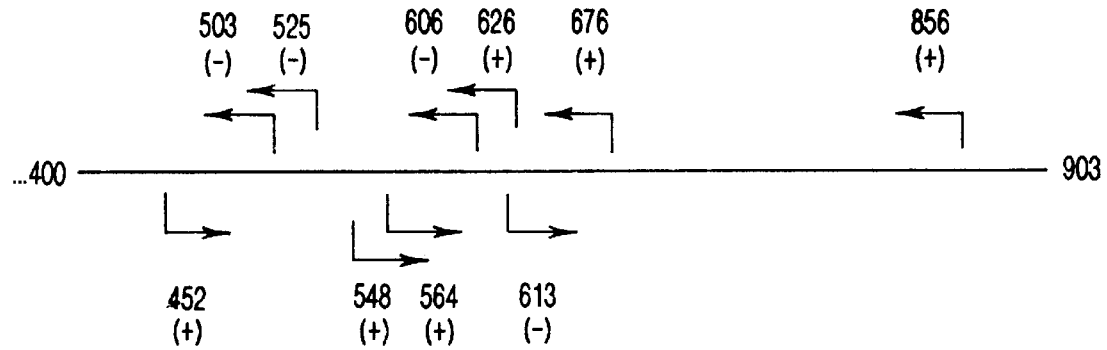
FIG-3

(2) INFORMATION FOR SEQ ID NO: 1:
  (i) SEQUENCE CHARACTERISTICS:
    (A) LENGTH: 904 amino acids
    (B) TYPE: HSV-1 glycoprotein B
    (D) TOPOLOGY: linear
    (K) RELEVANT RESIDUES IN SEQ ID NO. 1: 14-110; 295-507; 814-901

(xi) SEQUENCE DESCRIPTION: SEQ ID NO:1:

```
Met Arg Gln Gly Ala Pro Ala Arg Gly Arg Arg Trp Phe Val Val Trp
              5               10                  15

Ala Leu Leu Gly Leu Thr Leu Gly Val Leu Val Ala Ser Ala Ala Pro
            20                  25              30

Ser Ser Pro Gly Thr Pro Gly Val Ala Ala Ala Thr Gln Ala Ala Asn
          35                40                  45

Gly Gly Pro Ala Thr Pro Ala Pro Pro Ala Pro Gly Ala Pro Pro Thr
      50              55                  60

Gly Asp Pro Lys Pro Lys Lys Asn Arg Lys Pro Lys Pro Pro Lys Pro
 65             70                  75                      80

Pro Arg Pro Ala Gly Asp Asn Ala Thr Val Ala Ala Gly His Ala Thr
                  85                  90              95

Leu Arg Glu His Leu Arg Asp Ile Lys Ala Glu Asn Thr Asp Ala Asn
              100                 105                 110

Phe Tyr Val Cys Pro Pro Pro Thr Gly Ala Thr Val Val Gln Phe Glu
              115                 120                 125

Gln Pro Arg Arg Cys Pro Thr Arg Pro Glu Gly Gln Asn Tyr Thr Glu
        130                 135                 140

Gly Ile Ala Val Val Phe Lys Glu Asn Ile Ala Pro Tyr Lys Phe Lys
145                 150                 155                 160

Ala Thr Met Tyr Tyr Lys Asp Val Thr Val Ser Gln Val Trp Phe Gly
                165                 170                 175

His Arg Tyr Ser Gln Phe Met Gly Ile Phe Glu Asp Arg Ala Pro Val
            180                 185                 190

Pro Phe Glu Glu Val Ile Asp Lys Ile Asn Ala Lys Gly Val Cys Arg
        195                 200                 205

Ser Thr Ala Lys Tyr Val Arg Asn Asn Leu Glu Thr Thr Ala Phe His
210                 215                 220

Arg Asp Asp His Glu Thr Asp Met Glu Leu Lys Pro Ala Asn Ala Ala
225                 230                 235                 240

Thr Arg Thr Ser Arg Gly Trp His Thr Thr Asp Leu Lys Tyr Asn Pro
                245                 250                 255

Ser Arg Val Glu Ala Phe His Arg Tyr Gly Thr Thr Val Asn Cys Ile
            260                 265                 270

Val Glu Glu Val Asp Ala Arg Ser Val Tyr Pro Tyr Asp Glu Phe Val
        275                 280                 285

Leu Ala Thr Gly Asp Phe Val Tyr Met Ser Pro Phe Tyr Gly Tyr Arg
    290                 295                 300
```

FIG-4a

```
Glu Gly Ser His Thr Glu His Thr Ser Tyr Ala Ala Asp Arg Phe Lys
305                 310                 315                 320

Gln Val Asp Gly Phe Tyr Ala Arg Asp Leu Thr Thr Lys Ala Arg Ala
            325                 330                 335

Thr Ala Pro Thr Thr Arg Asn Leu Leu Thr Thr Pro Lys Phe Thr Val
            340                 345                 350

Ala Trp Asp Trp Val Pro Lys Arg Pro Ser Val Cys Thr Met Thr Lys
        355                 360                 365

Trp Gln Glu Val Asp Glu Met Leu Arg Ser Glu Tyr Gly Gly Ser Phe
    370                 375                 380

Arg Phe Ser Ser Asp Ala Ile Ser Thr Thr Phe Thr Thr Asn Leu Thr
385                 390                 395                 400

Glu Tyr Pro Leu Ser Arg Val Asp Leu Gly Asp Cys Ile Gly Lys Asp
            405                 410                 415

Ala Arg Asp Ala Met Asp Arg Ile Phe Ala Arg Arg Tyr Asn Ala Thr
            420                 425                 430

His Ile Lys Val Gly Gln Pro Gln Tyr Tyr Leu Ala Asn Gly Gly Phe
        435                 440                 445

Leu Ile Ala Tyr Gln Pro Leu Leu Ser Asn Thr Leu Ala Glu Leu Tyr
    450                 455                 460

Val Arg Glu His Leu Arg Glu Gln Ser Arg Lys Pro Pro Asn Pro Thr
465                 470                 475                 480

Pro Pro Pro Pro Gly Ala Ser Ala Asn Ala Ser Val Glu Arg Ile Lys
            485                 490                 495

Thr Thr Ser Ser Ile Glu Phe Ala Arg Leu Gln Phe Thr Tyr Asn His
            500                 505                 510

Ile Gln Arg His Val Asn Asp Met Leu Gly Arg Val Ala Ile Ala Trp
        515                 520                 525

Cys Glu Leu Gln Asn His Glu Leu Thr Leu Trp Asn Glu Ala Arg Lys
530                 535                 540

Leu Asn Pro Asn Ala Ile Ala Ser Ala Thr Val Gly Arg Arg Val Ser
545                 550                 555                 560

Ala Arg Met Leu Gly Asp Val Met Ala Val Ser Thr Cys Val Pro Val
            565                 570                 575

Ala Ala Asp Asn Val Ile Val Gln Asn Ser Met Arg Ile Ser Ser Arg
            580                 585                 590

Pro Gly Ala Cys Tyr Ser Arg Pro Leu Val Ser Phe Arg Tyr Glu Asp
        595                 600                 605

Gln Gly Pro Leu Val Glu Gly Gln Leu Gly Glu Asn Asn Glu Leu Arg
    610                 615                 620

Leu Thr Arg Asp Ala Ile Glu Pro Cys Thr Val Gly His Arg Arg Tyr
625                 630                 635                 640

Phe Thr Phe Gly Gly Gly Tyr Val Tyr Phe Glu Glu Tyr Ala Tyr Ser
            645                 650                 655

His Gln Leu Ser Arg Ala Asp Ile Thr Thr Val Ser Thr Phe Ile Asp
            660                 665                 670
```

FIG-4b

```
Leu Asn Ile Thr Met Leu Glu Asp His Glu Phe Val Pro Leu Glu Val
        675             680                 685
Tyr Thr Arg His Glu Ile Lys Asp Ser Gly Leu Leu Asp Tyr Thr Glu
    690             695                 700
Val Gln Arg Arg Asn Gln Leu His Asp Leu Arg Phe Ala Asp Ile Asp
705             710                 715                     720
Thr Val Ile His Ala Asp Ala Asn Ala Ala Met Phe Ala Gly Leu Gly
            725                 730                 735
Ala Phe Phe Glu Gly Met Gly Asp Leu Gly Arg Ala Val Gly Lys Val
            740             745                 750
Val Met Gly Ile Val Gly Gly Val Val Ser Ala Val Ser Gly Val Ser
        755             760                 765
Ser Phe Met Ser Asn Pro Phe Gly Ala Leu Ala Val Gly Leu Leu Val
770                 775                 780
Leu Ala Gly Leu Ala Ala Ala Phe Phe Ala Phe Arg Tyr Val Met Arg
785             790                 795                     800
Leu Gln Ser Asn Pro Met Lys Ala Leu Tyr Pro Leu Thr Thr Lys Glu
            805                 810                 815
Leu Lys Asn Pro Thr Asn Pro Asp Ala Ser Gly Glu Gly Glu Glu Gly
            820                 825                 830
Gly Asp Phe Asp Glu Ala Lys Leu Ala Glu Ala Arg Glu Met Ile Arg
        835                 840                 845
Tyr Met Ala Leu Val Ser Ala Met Glu Arg Thr Glu His Lys Ala Lys
    850                 855                 860
Lys Lys Gly Thr Ser Ala Leu Leu Ser Ala Lys Val Thr Asp Met Val
865                 870                 875                     880
Met Arg Lys Arg Arg Asn Thr Asn Tyr Thr Gln Val Pro Asn Lys Asp
                885                 890                 895
Gly Asp Ala Asp Glu Asp Leu
            900         904
```

FIG-4c (2) INFORMATION FOR SEQ ID NO: 2:
(i) SEQUENCE CHARACTERISTICS:
(A) LENGTH: 904 amino acids
(B) TYPE: HSV-2 glycoprotein B
(D) TOPOLOGY: linear
(K) RELEVANT RESIDUES IN SEQ ID NO. 2: 18-75; 819-904

(xi) SEQUENCE DESCRIPTION: SEQ ID NO:2:

```
Met Arg Gly Gly Gly Leu Ile Cys Ala Leu Val Val Gly Ala Leu Val
                5                   10                  15

Ala Ala Val Ala Ser Ala Ala Pro Ala Ala Pro Ala Ala Pro Arg Ala
            20                  25                  30

Ser Gly Gly Val Ala Ala Thr Val Ala Ala Asn Gly Gly Pro Ala Ser
        35                  40                  45

Arg Pro Pro Pro Val Pro Ser Pro Ala Thr Thr Lys Ala Arg Lys Arg
    50                  55                  60

Lys Thr Lys Lys Pro Pro Lys Arg Pro Glu Ala Thr Pro Pro Pro Asp
65                  70                  75                  80

Ala Asn Ala Thr Val Ala Ala Gly His Ala Thr Leu Arg Ala His Leu
                85                  90                  95

Arg Glu Ile Lys Val Glu Asn Ala Asp Ala Gln Phe Tyr Val Cys Pro
            100                 105                 110

Pro Pro Thr Gly Ala Thr Val Val Gln Phe Glu Gln Pro Arg Arg Cys
        115                 120                 125

Pro Thr Arg Pro Glu Gly Gln Asn Tyr Thr Glu Gly Ile Ala Val Val
    130                 135                 140

Phe Lys Glu Asn Ile Ala Pro Tyr Lys Phe Lys Ala Thr Met Tyr Tyr
145                 150                 155                 160

Lys Asp Val Thr Val Ser Gln Val Trp Phe Gly His Arg Tyr Ser Gln
                165                 170                 175

Phe Met Gly Ile Phe Glu Asp Arg Ala Pro Val Pro Phe Glu Glu Val
            180                 185                 190

Ile Asp Lys Ile Asn Ala Lys Gly Val Cys Arg Ser Thr Ala Lys Tyr
        195                 200                 205

Val Arg Asn Asn Met Glu Thr Thr Ala Phe His Arg Asp Asp His Glu
    210                 215                 220

Thr Asp Met Glu Leu Lys Pro Ala Lys Val Ala Thr Arg Thr Ser Arg
225                 230                 235                 240

Gly Trp His Thr Thr Asp Leu Lys Tyr Asn Pro Ser Arg Val Glu Ala
                245                 250                 255

Phe His Arg Tyr Gly Thr Thr Val Asn Cys Ile Val Glu Glu Val Asp
            260                 265                 270

Ala Arg Ser Val Tyr Pro Tyr Asp Glu Phe Val Leu Ala Thr Gly Asp
        275                 280                 285

Phe Val Tyr Met Ser Pro Phe Tyr Gly Tyr Arg Glu Gly Ser His Thr
    290                 295                 300
```

FIG-5a

```
Glu His Thr Ser Tyr Ala Ala Asp Arg Phe Lys Gln Val Asp Gly Phe
305                 310                 315                 320
Tyr Ala Arg Asp Leu Thr Thr Lys Ala Arg Ala Thr Ser Pro Thr Thr
                325                 330                 335
Arg Asn Leu Leu Thr Thr Pro Lys Phe Thr Val Ala Trp Asp Trp Val
                340                 345                 350
Pro Lys Arg Pro Ala Val Cys Thr Met Thr Lys Trp Gln Glu Val Asp
            355                 360                 365
Glu Met Leu Arg Ala Glu Tyr Gly Gly Ser Phe Arg Phe Ser Ser Asp
    370                 375                 380
Ala Ile Ser Thr Thr Phe Thr Thr Asn Leu Thr Gln Tyr Ser Leu Ser
385                 390                 395                 400
Arg Val Asp Leu Gly Asp Cys Ile Gly Arg Asp Ala Arg Glu Ala Ile
                405                 410                 415
Asp Arg Met Phe Ala Arg Lys Tyr Asn Ala Thr His Ile Lys Val Gly
            420                 425                 430
Gln Pro Gln Tyr Tyr Leu Ala Thr Gly Gly Phe Leu Ile Ala Tyr Gln
        435                 440                 445
Pro Leu Leu Ser Asn Thr Leu Ala Glu Leu Tyr Val Arg Glu Tyr Met
    450                 455                 460
Arg Glu Gln Asp Arg Lys Pro Arg Asn Ala Thr Pro Ala Pro Leu Arg
465                 470                 475                 480
Glu Ala Pro Ser Ala Asn Ala Ser Val Glu Arg Ile Lys Thr Thr Ser
                485                 490                 495
Ser Ile Glu Phe Ala Arg Leu Gln Phe Thr Tyr Asn His Ile Gln Arg
            500                 505                 510
His Val Asn Asp Met Leu Gly Arg Ile Ala Val Ala Trp Cys Glu Leu
        515                 520                 525
Gln Asn His Glu Leu Thr Leu Trp Asn Glu Ala Arg Lys Leu Asn Pro
530                 535                 540
Asn Ala Ile Ala Ser Ala Thr Val Gly Arg Arg Val Ser Ala Arg Met
545                 550                 555                 560
Leu Gly Asp Val Met Ala Val Ser Thr Cys Val Pro Val Ala Pro Asp
                565                 570                 575
Asn Val Ile Val Gln Asn Ser Met Arg Val Ser Ser Arg Pro Gly Thr
            580                 585                 590
Cys Tyr Ser Arg Pro Leu Val Ser Phe Arg Tyr Glu Asp Gln Gly Pro
        595                 600                 605
Leu Ile Glu Gly Gln Leu Gly Glu Asn Asn Glu Leu Arg Leu Thr Arg
    610                 615                 620
Asp Ala Leu Glu Pro Cys Thr Val Gly His Arg Arg Tyr Phe Ile Phe
625                 630                 635                 640
Gly Gly Gly Tyr Val Tyr Phe Glu Glu Tyr Ala Tyr Ser His Gln Leu
                645                 650                 655
Ser Arg Ala Asp Val Thr Thr Val Ser Thr Phe Ile Asp Leu Asn Ile
            660                 665                 670
```

FIG-5 b

```
Thr Met Leu Glu Asp His Glu Phe Val Pro Leu Glu Val Tyr Thr Arg
        675                 680                 685
His Glu Ile Lys Asp Ser Gly Leu Leu Asp Tyr Thr Glu Val Gln Arg
    690                 695                 700
Arg Asn Gln Leu His Asp Leu Arg Phe Ala Asp Ile Asp Thr Val Ile
705                 710                 715                 720
Arg Ala Asp Ala Asn Ala Ala Met Phe Ala Gly Leu Cys Ala Phe Phe
                725                 730                 735
Glu Gly Met Gly Asp Leu Gly Arg Ala Val Gly Lys Val Val Met Gly
            740                 745                 750
Val Val Gly Gly Val Val Ser Ala Val Ser Gly Val Ser Ser Phe Met
        755                 760                 765
Ser Asn Pro Phe Gly Ala Leu Ala Val Gly Leu Leu Val Leu Ala Gly
    770                 775                 780
Leu Val Ala Ala Phe Phe Ala Phe Arg Tyr Val Leu Gln Leu Gln Arg
785                 790                 795                 800
Asn Pro Met Lys Ala Leu Tyr Pro Leu Thr Thr Lys Glu Leu Lys Thr
                805                 810                 815
Ser Asp Pro Gly Gly Val Gly Gly Glu Gly Glu Gly Ala Glu Gly
            820                 825                 830
Gly Gly Phe Asp Glu Ala Lys Leu Ala Glu Ala Arg Glu Met Ile Arg
        835                 840                 845
Tyr Met Ala Leu Val Ser Ala Met Glu Arg Thr Glu His Lys Ala Arg
    850                 855                 860
Lys Lys Gly Thr Ser Ala Leu Leu Ser Ser Lys Val Thr Asn Met Val
865                 870                 875                 880
Leu Arg Lys Arg Asn Lys Ala Arg Tyr Ser Pro Leu His Asn Glu Asp
                885                 890                 895
Glu Ala Gly Asp Glu Asp Glu Leu
            900             904
```

FIG-5c

IMMUNOASSAY FOR HERPES SIMPLEX VIRUS

CROSS-REFERENCE TO RELATED APPLICATIONS

This application is a continuation-in-part of application of U.S. patent application Ser. No. 08/426,604, filed on Apr. 21, 1995, and the specification thereof is incorporated herein be reference.

BACKGROUND OF THE INVENTION

The invention relates to glycoprotein B segments of herpes simplex virus types 1 and 2 (HSV-1, HSV-2) containing linear antigenic epitopes reactive with human antibodies to HSV-1 and HSV-2. Of particular interest are HSV glycoprotein B segments containing type-specific epitopes useful in serodiagnostic immunoassays for distinguishing HSV-1 infection from HSV-2 in humans, and in human vaccines for generating neutralizing antibodies to HSV-1 or HSV-2.

1. Field of Art

The herpes simplex virus (HSV) glycoprotein B (gB) is a transmembrane envelope glycoprotein that contributes to the penetration of virions into host cells by host cell recognition, viral adherence, and virion-cell membrane fusion. gB induces fusion of the virion envelope with the cellular cytoplasmic membrane, an essential function for virus entry. Immunization of humans and animals with purified gB induces virus-neutralizing antibody responses, and recombinant gB proteins are being investigated as HSV vaccines. The amino acid sequences for both gB-1 and gB-2 and their encoding nucleotide sequences are known and available, e.g., from Genebank.

The HSV type 2 gB (gB-2) polypeptide contains 904 amino acids (aa)—(FIG. 5). The amino-terminal segment (1–22aa) is a signal peptide that is cleaved from the mature protein during processing. aa 745 to 798 constitute a hydrophobic transmembrane anchor domain. The segment carboxy-proximal to the anchor domain (aa 799 to 904) is cytoplasmic and appears to mediate membrane fusion. The amino-proximal segment (aa 23 to 744) is extracellular and contains epitopes that are recognized by virus-neutralizing antibodies. HSV type 1 gB (gB-1) is structurally similar (FIG. 4).

HSV-2 and HSV-1 are closely related viruses. Most of their proteins, including gB, are highly conserved (very homologous) and are known to elicit cross-reactive antibody responses. It has accordingly been difficult to provide reliable, sensitive immunoassays capable of distinguishing HSV-1 from HSV-2 infection, or to provide type-specific vaccines effective against HSV infection.

2. Discussion of Related Art

HSV infections in humans are commonly diagnosed by immunoassay of blood samples for HSV antibodies in Western blot assays or other immunoassays using random lysates of cells infected with HSV-1 or HSV-2 as antigen targets. These serodiagnostic assays have been recognized as generally unsatisfactory for distinguishing HSV-1 infection from HSV-2 infection owing to strong responses of type-common antibody-reactive regions of both native proteins. This has proved to be a particular problem in distinguishing acute HSV-2 infection in patients previously infected with HSV-1, because of a likely anamnestic response to HSV-1 and HSV-2 type-common antigens which obscures responses to type-specific antigens. Difficulties in detecting HSV-2 type-specific antibodies by using HSV-2 cell lysate Western blot assays on subjects previously infected with HSV-1, for example, may result in a not uncommon misclassification of samples subjected to these assays as HSV-1 positive and HSV-2 negative. Accordingly, on-going research has attempted to identify domains of various native HSV viral proteins which are highly reactive with anti HSV-1 and anti HSV-2 antibodies and which provide a virus type-specific antibody response.

While several HSV proteins have been considered as sources of useful antigenic epitopes for diagnosis and prevention, only HSV-1 and HSV-2 glycoprotein G (gG-1, gG-2) has been found useful to date for use in assays with improved sensitivities and specificities. Most HSV-2 and HSV-1 proteins are very homologous, as noted above. However, HSV-2 gG-2 and HSV-1 gG-1 have highly dissimilar amino acid sequences, and human gG-2 and gG-1 antibody responses in the presence of HSV-2 and HSV-1 infections appear to have significantly improved virus type-specificity over lysates of infected cells. Thus, detection of antibody reactivities to native or recombinant HSV-1 or HSV-2 glycoprotein G presently forms the basis for current HSV type-specific immunoassays.

HSV glycoprotein B has also sparked interest as a possible source of type-specific HSV antigens. To date, however, only the complete proteins have been used, and these have exhibited only cross-reactive antibody responses. Virus-specific determinates to human antibodies have been eagerly sought for many years, without notable success.

HSV-2 and HSV-1 infections each elicit strong immunoglobulin G (IgG) antibody responses in vivo to both HSV-2 gB-2 and to HSV-1 gB-1 (1, 2, 3); these antibodies are detectable early in acute infections, attain high titers, and persist for many years (4, 2, 5). Cross-reactive polyclonal antibody responses predominate (4, 6, 7). This exhibition of the related antigenicity of HSV gB-2 and gB-1 is consistent with the marked overall conservation of their amino acid sequences (86% at the amino acid level). Perhaps in consequence, the structures of gB-1 and gB-2 have not been previously broadly elucidated with respect to specific antigenic domains recognizing human antibodies which are clinically useful, especially type-specific antigenic regions capable of distinguishing HSV-1 from HSV-2 infection.

While human IgG antibodies cross-reactive to whole or randomly lysed gB-2 and gB-1 are thus known, virus type-specific antibodies have only been reported in murine models. Immunization of laboratory animals with purified virion-derived gB-2 elicits antibodies that neutralize HSV-2 infectivity in vitro and protect susceptible animal hosts from experimental HSV-2 infections (reviewed in *Seminars in Pediatric Infections* 2: 178–185, Stanberry, 1991 and *Microbiol. and Immunol.* 179: 137–158, Burke, 1992).

HSV-2 infections and HSV-1 infections elicit strong IgG antibody responses to gB-2 and to gB-1, respectively. gB-2 responses include antibodies that cross-react strongly with native gB-1, and gB-1 responses include antibodies that cross-react strongly with native gB-2. Therefore, gB-2 reactivities and gB-1 reactivities do not differentiate between antibody responses to HSV-2 infections and antibody responses to HSV-1 infections. Immune responses to most HSV-2 proteins include antibodies that cross-react with the homologous HSV-1 protein, and vice versa. Linear epitopes that react with type-specific, virus-neutralizing murine monoclonal antibodies have been localized to the extracellular amino-terminal segment of gB-1 (8, 9, 10, 11, 12, 13, 14). However, little information has been available regarding the locations and type specificities of gB epitopes recognized by human HSV antibodies (8, 15, 14). Vaccines comprising both recombinant gB-2 and gB-2 are currently undergoing clinical trials (16, 17), but efficacy or type-specificity of gB-2 in this application is not yet known.

The above numerals refer to the following publications, all incorporated herein by reference:
1. *J. Virol. Methods* 18:159–168, 1987
2. *Infect. Immun.* 31:1062–1070, 1981
3. *Am. J. Epi* 104:192–201, 1976
4. *J. Med. Virol.* 17:153–166, 1985
5. *Infect. Immunol.* 34:880–887, 1981
6. *J. Med. Virol.* 15:251–263, 1985
7. *Rev. Infect. Dis.* 2:899–913, 1980
8. *J. Med. Virol.* 27:309–316, 1989
9. *J. Gen. Virol.* 70:735–741, 1989
10. *Virol.* 135:379–394, 1984
11. *Virol.* 186:99–112, 1992
12. *Virol.* 172:11–24, 1989
13. *J. Infect. Dis.* 166:623–627, 1992
14. *J. Infect Dis.* 168:844–853, 1993
15. *J. Clin. Micro.* 23:725–730, 1986
16. *Rev. Infect. Dis.* 13:S906–S911, 1991
17. *Micro. Immunol.* 179:137–158, 1992

SUMMARY OF THE DISCLOSURE

The invention accordingly provides linear (continuous) glycoprotein B-1 and B-2 polypeptide segments each containing at least one antigenic epitope which reacts with human HSV-1 or HSV-2 antibodies in a virus type-specific manner and which is isolated from polypeptide segments containing linear binding sites cross-reactive with HSV-1 and HSV-2 human antibodies. The type-specific epitopes are useful in immunoassays for distinguishing HSV-1 and HSV-2 infections in humans. The invention further provides cross-reactive linear epitopes of HSVgB-1 and gB-2 isolated from type-specific epitopes useful in immuno diagnosis of both HSV-1 and HSV-2 infection in humans.

According to the invention, an amino-proximal gB-2 segment between aa 18 and 75 reacts preferentially with HSV-2 human antibodies, and a carboxy-terminal gB-2 segment between aa 819 and 904 reacts strongly with both HSV-2 and HSV-1 human antibodies. In experiments to date, the gB-2 18–75 aa segment has been found to be up to 100% specific to HSV-2 antibodies, with no recognition of HSV-1 antibodies in the serodiagnostic assays employed.

Also according to the invention, gB-1 polypeptide segments between aa 14 and 110 and between aa 295 and 507 react preferentially with HSV-1 human antibodies, and a gB-1 carboxy-terminal segment between aa 814–901 strongly cross-reacts with human antibodies to both HSV-1 and HSV-2.

The gB-2 type-specific segment (aa 18–75) is particularly useful for diagnosing acute HSV-2 infection in patients previously infected with HSV-1, as this segment reacts strongly with human IgM antibodies which appear in the very early stages of infection, as well as later-appearing IgG. The cross-reactive gB-2 segment aa 819–904 is especially useful in diagnosing acute HSV-1 and HSV-2 infections, as it too reacts strongly with IgM human antibodies, in contrast to the disclosed gB-1 cross-reactive segments which are also diagnostic of human HSV IgG antibodies, but not IgM.

All the described epitopes are useful in vaccines for generating virus-neutralizing anti-HSV antibodies in humans.

While the polypeptide or oligopeptide segments described herein can be synthesized by known techniques or obtained from native HSV gB-1 or gB-2, it is preferred that the peptides be obtained as fusion proteins expressed by suitable host cells such as *E. coli.* DNA sequences encoding the amino acid sequences of the invention are described or are readily obtained from known databases such as Genebank for the desired constructs.

BRIEF DESCRIPTION OF THE DRAWING

FIG. 1. Type-specific and cross-reactive regions of gB-2. The panels at the top of the figure are replicate Western blots. The blot on the left was reacted with human serum that contained HSV-2 antibodies and does not contain HSV-1 antibodies. The antibodies reacted with the pGB2-SS2 protein, with the pGB2-AP2 protein, and with the pGB2-SS1 protein. The middle panel was reacted with a serum sample that contained HSV-1 antibodies and did not contain HSV-2 antibodies. The antibodies reacted with the pGB2-SS2 protein and did not react with the pGB2-SS1 or the pGB2-AP2 proteins. The blot on the right was reacted with a serum sample that contained neither HSV-1 antibodies nor HSV-2 antibodies. There was no reactivity with any of the gB-2 recombinant proteins.

FIGS. 2A and B. Mapping of the gB-2 region that reacts with HSV-2 antibodies in a virus type-specific manner. A nested set of carboxy-to-amino terminus deletions was made in the pGB2-SS2 construct. The nested deletions were reacted with two serum samples that contained HSV-2 antibodies.

FIGS. 3A through D. Mapping of the gB-2 region that reacts with both HSV-2 antibodies and with HSV-1 antibodies. Panels A contain a nested set of amino-to-carboxy terminus deletions in the pGB2-SS1 construct. Panels B contain a nested set of carboxy-to-amino terminus deletions in the pGB2-SS1 construct. These nested deletions were reacted with a serum sample that contained HSV-1 antibodies and did not contain HSV-2 antibodies (top panels), and with a serum sample that contained HSV-2 antibodies and did not contain HSV-1 antibodies (bottom panels). The antibody reactivities in each case map to the gB-2 aa 564 to 626 segment.

FIGS. 4*a*–4*c*. Amino acid sequence of HSV-1 glycoprotein B including segments 14–110; 295–507; and 814–901 isolated and characterized according to the invention.

FIGS. 5*a*–5*c*. Amino acid sequence of HSV-2 glycoprotein B including segments 18–75 and 819–904, isolated and characterized according to the invention.

FIG. 6. gB-2 functional domains and human antibody-reactive regions. The middle bar represents the gB-2 polypeptide. Bars A through D represent previously described functional domains: A, the signal sequence region; B, a segment that contains a rate of entry locus (56); C, the transmembrane anchor segment; and D, a region associated with membrane fusion. Human antibody-reactive regions are represented by bars E through H: E, the gB-2 segment from aa 18 to 75 that reacts preferentially with HSV-2 antibodies; H, the gB-2 carboxy-terminal segment from aa 819–904 recognized by all HSV-2 antibodies and by all HSV-1 cross-reactive antibodies; G, the gB-2 segment from aa 564 to 626 recognized by some HSV-2 antibodies and by some HSV-1 cross-reactive antibodies; and F a minor antigenic region recognized by some HSV-2 antibodies.

DETAILED DESCRIPTION OF THE INVENTION

In the description of the invention and the claims, the specific polypeptide segment sequences recited are deemed to include any substantially homologous segments (at least about 85% homology, preferably at least about 90% homology) which have substantially equivalent binding activity, including avidity and specificity. Preferably, immunogenicity of any altered sequence is not significantly increased. The segments of the invention include one or more linear binding sites, but may not define the minimum epitope recognized by HSV antibodies. Thus, as known in the art, one or more of the amino acids present in the claimed polypeptides may be deleted or altered without substantially compromising useful biological activity, and such polypeptides are within the scope of the claims.

Human gB-2 and gB-1 antibody responses were characterized by using gB-1 and gB-2 recombinant polypeptides as antigen targets in Western blot assays. Reactivities of HSV-2 antibodies to recombinant gB-2 polypeptides were compared with reactivities of HSV-1 antibodies to the same recombinant gB-2 polypeptides. The gB-2 response included antibodies that reacted with three different regions of the glycoprotein. Two of these regions also cross-reacted with HSV-1 IgG antibodies. However, an amino-proximal segment of gB-2 reacted with HSV-2 antibodies and did not react with HSV-1 antibodies. Therefore, although native gB-2 cannot be used to readily differentiate between HSV-2 antibodies and HSV-1 antibodies, the amino-proximal segment of gB-2 is recognized by HSV-2 antibodies in a type specific manner. This type specific gB-2 reactivity can complement serologic assays based upon gG-1 and gG-2. Similarly, it was found that gB-1 segments between aa 14–110 and between aa 295 to 507 reacted with HSV-1 antibodies but did not react with HSV-2 antibodies. These gB-1 and gB-2 recombinant polypeptides are useful reagents for the virus type-specific serodiagnosis of HSV-1 and HSV-2 infections.

HSV-2 gB-2 polypeptide segments comprising type-specific and type-common antigenic epitopes As discussed above, HSV-2 glycoprotein B includes an epitope in the amino proximal region that reacts with human antibodies in a type-specific manner, and an epitope in the carboxy terminal region that cross-reacts with both HSV-1 and HSV-2 antibodies.

Recombinant polypeptides representing three different segments of herpes simplex virus type 2 glycoprotein B were tested for human IgG antibody reactivities. The constructs encompassed an amino proximal portion (gB2 SS2) including amino acids 18 to 228, a mid portion (gB2 AP2) including amino acids 154 to 503, and a carboxy-terminal segment (gB2-SS1) including amino acids 228–903 (Table 1). These recombinant proteins were used as antigen targets in Western immunoblot assays. Serum samples from 45 individuals with known HSV serotypes by HSV type-specific glycoprotein G tests were evaluated. GB2 SS2 was strongly reactive with 15 of 15 serum samples from HSV 2+/1− individuals. In contrast, 0 of 15 HSV 1+/2− serum samples, and 0 of 15 HSV 1−/2− serum samples were reactive. GB2 AP2 reactivity was seen in 5 of 15 HSV 2+/1− serum samples, 0 of 15 HSV 1+/2− serum samples, and 0 of 15 HSV 1−/2− serum samples. Lastly, gB2 SS1 reactivity was seen in 15 of 15 HSV 2+/1− serum samples, 15 of 15 HSV 1+/2− and 0 of 15 HSV 1−/2− serum samples.

Thus, HSV gB2 includes an epitope in the amino proximal region that strongly reacts with HSV 2 antibodies, and an epitope in the carboxyl terminal region that strongly reacts with both HSV 1 and HSV 2 antibodies. In contrast, previous HSV serotyping relying upon immunoblotting with whole viral lysate or type specific glycoprotein G assays has typically provided uncertain results.

HSV gB-2 and gB-1 polypeptide segments comprising type-specific and type-common antigenic epitopes Segments of the herpes simplex virus type 2 (HSV-2) glycoprotein B (gB-2) gene and the herpes virus type 1 (HSV-1) glycoprotein B (gB-1) were expressed as recombinant proteins in *Escherichia coli* and were used to detect human immunoglobulin-G (IgG) reactivities in Western blot (immunoblot) assays. Human serum samples that contained HSV-2 antibodies (n=56), that contained herpes simplex virus type 1 (HSV-1) antibodies (n=33), and that contained no HSV IgG antibodies (n=32) were tested. HSV-1 antibodies and HSV-2 antibodies were detected by using viral lysates of HSV-1 and HSV-2 as antigen targets. Virus type specificities were defined on the basis of antibody reactivities to native HSV-1 glycoprotein G (gG-1) and to native HSV-2 glycoprotein G (gG-2), respectively, in Western blot assays. HSV-2 IgG antibodies reacted strongly with a gB-2 amino-proximal segment that included amino acids (aa) 18 to 75; HSV-1 IgG antibodies did not react with this region. Both HSV-2 antibodies and HSV-1 antibodies reacted strongly with a carboxy-terminal gB-2 segment from aa 819 to 904. HSV-2 antibodies, and some HSV-1 cross-reactive antibodies, recognized a gB-2 region between aa 564 and 626. A gB-1 segment from aa 14–110 and another from aa 295 to 507 reacted with HSV-1 antibodies but did not react with HSV-2 antibodies.

HSV-1 gB-1 polypeptide segments comprising type-specific and type-common antigenic epitopes Human antibody responses to gB-1 were also characterized by using gB-1 recombinant polypeptides as antigen targets in Western blot assays as described above. gB-1 responses included two regions that reacted with human antibodies in a type-specific manner. These include a strong HSV-1 type-specific region in the amino terminus that includes aa 14–110, and a less strongly reactive type-specific region included within aa 295–507 (above). Similar to the cross-reactive carboxy terminal region of gB-2, the carboxy terminal portion of gB-1 is cross-reactive with HSV-1 and HSV-2 antibodies. This region is included within aa 814–901.

Utility of HSV gB polypeptide segments

The antigenic epitopes within the HSV gB polypeptide segments described herein are useful in the serodiagnosis of HSV infection in humans by immunoassay techniques well-known in the art. The gB-2 aa 18 to 75 segment thus is a very useful reagent for defining antibody responses elicited by HSV-2 infections, particularly acute HSV-2 infections as described above. Similarly, gB-1 aa 14–110 and 295 to 507 segments are useful reagents for defining antibody responses elicited by HSV-1 infections. The cross-reactive epitopes included within gB1 aa 815–901 and gB2 aa 819–904 are useful reagents for serodiagnosis at HSV.

The antigenic epitopes are further useful in vaccines for eliciting neutralizing antibodies in humans. The vaccines are formulated as known in the art, for example using the adjuvant and dosages now used in other HSV glycoprotein vaccines such as those described in detail in *Reviews of Infectious Diseases* and *Microbiol. and Immunol., op. cit.*

EXAMPLES

MATERIALS AND METHODS

Human subjects. Human serum samples were obtained from three sources. Forty serum samples were obtained from participants in a phase 11 clinical trial evaluating the immunogenic properties of recombinant gB-2 and gD-2 vaccines. Samples were obtained from these subjects prior to the administration of the HSV-2 vaccines. Subjects were identified as having serum IgG antibodies to neither HSV-1 nor HSV-2 (HSV 1−/2−) (n=23), or as having serum IgG antibodies to HSV-1 and not HSV-2 (HSV 1+/2−) (n=17). Sixty-three serum samples were obtained from volunteers who were screened for participation in a phase III clinical trial evaluating the efficacy of a recombinant gB-2 plus gD-2 vaccine (HRRC 92–146; 93–185 and Burke 1991, 1992 op.cit.). The subjects included 9 subjects who were HSV 1−/2−, 16 subjects who were HSV 1+/2−, 21 subjects who had antibodies to HSV-2 and not HSV-1 (HSV 1−/2+), and 17 subjects who had antibodies to both HSV-1 and HSV-2 (HSV 1+/2+). Eighteen additional serum samples that had previously been characterized as at the University of Washington as HSV1−/2+ were tested.

Definition of HSV-1 and HSV-2 antibody responses. Serum HSV antibodies were detected by using viral lysates of HSV-1 and HSV-2 as antigen targets in Western blot assays. HSV-1 antibody responses were defined by the presence of native gG-1 reactivity in HSV-1 viral lysates by Western blot assay. HSV-2 antibody responses were defined by the presence of native gG-2 reactivity in HSV-2 viral lysates by Western blot assay.

Expression plasmid constructs. gB-2 DNA-encoded polypeptides were expressed in *Escherichia coli* HB101 by using the pATH expression plasmids (Koerner ref.). Expression vectors pATH1, pATH10, pATH 11, pATH20, pATH21, pATH22 and pATH23 were obtained from the American Type Culture Collection (ATCC 37695 through 37703, respectively). pATH vectors contain 5' transcription control elements and a portion of the first structural gene (trpE) of the *E. coli* tryptophan synthetase operon. HSV-2 gB DNA segments were inserted into pATH DNA at restriction enzyme sites within a polylinker segment located 3' to the trpE gene. HSV-2 gB DNA-encoded polypeptides were expressed as fusion proteins linked to a 37,000-Da polypeptide encoded by trpE.

gB-2 DNA segments were derived from plasmid pHS218 (Stuve 1987), which contains the entire gB-2 coding sequence. Three overlapping expression constructs were made that included the amino-proximal portion (pGB2-SS2), the midportion (pGB2-AP2), and the carboxy-proximal portion (pGB2-SS1) of gB-2. For pGB2-SS2, pHS218 DNA was digested with SacI and SacII, and the gB-2 DNA segment from nucleotide (nt) 50 to 716 was ligated to vector pBluescript 11 KS+ (Stratagene, La Jolla, Calif.) DNA (SacI-SacII digest). gB-2 nucleotide coordinates are numbered starting from the first methionine codon. The pBluescript-gB2 recombinant plasmid was digested with BamHI and SacI, and the gB-2 DNA-containing insert was ligated to pATH23 DNA (BamHI-SacI digest). For pGB2-AP2, pHS218 was digested with ApoI and PstI, and the gB-2 nt 407 to 1511 fragment was ligated to pATH20 DNA (EcoRI-PstI digest). For pGB2-SS1, pHS218 was digested with SacI, and the gB-2 nt 716 to 2711 fragment was ligated to pATH20 DNA (SacI digest). Additional gB-2 expression plasmids were constructed in order to further define antibody-reactive regions. Plasmid pGB2-HA1 was constructed by digesting pGB2-SS2 DNA with HindIII and ApoI, and the gB-2 nt 50 to 407 fragment was ligated to pATH23 DNA (HindIII-EcoRI digest). For pGB2-SST, pGB2-SS2 DNA was digested with Sty1, removing a 417 bp DNA fragment from the midportion of SS2. The truncated plasmid was then relegated. Plasmid pGB2-SP1 was generated by digesting pGB2-SS1 DNA with Pst1, removing the gB-2 nt 1511 to 2711 fragment, and relegating the plasmid DNA ends. Plasmid pGB2-SX0 was constructed by digesting pGB2-SS1 DNA with Xho1 and BamHI, and removing the gB-2 nt 1879 to 2711 fragment. The ends of the plasmid DNA were made blunt by digesting with nuclease S1, and the blunted ends were relegated. Plasmid pGB2-SMB was generated by digesting pHS218 with Sma1 and BamH1, and the gB-2 nt 2454 to 3164 fragment was ligated to pATH10 DNA (Sma1-BamH1 digest). Plasmid pGB1 NSP1 was generated by digesting plasmid pHS108 with NspI, and ligating the HSV-1 fragment to pATH23 (SphI digest). The recombinant plasmid was digested with PstI, and the HSV-1 DNA-containing fragment was ligated to pATH21 (PstI digest). Recombinant DNAs were sequenced across the pATH-HSV gB-2 junction to confirm that the gB2 fragments were inserted in the desired reading frame orientation.

Exonuclease III and nuclease S1 deletion constructs. Antibody-reactive regions of the recombinant proteins were mapped by generating nested sets of deletion clones. Unidirectional 3'-to-5' DNA deletions were made in the gB-2 inserts of expression plasmids pGB2-SS2 and pGB2-SS1. Deletions were made by digesting linearized plasmids DNAs with exonuclease III (exoIII) and nuclease S1 according to the protocol of Henikoff (Henikoff 1984). pGB2-SS2 DNA was prepared for exoIII-nuclease S1 deletions by cleavage at StyI and SacI sites within the gB-2 DNA insert. pGB2-SS1 DNA was prepared for exoIII-nuclease S1 deletion by cleavage at NcoI and KpnI sites within the pATH20 polylinker. In order to generate 5'-to-3' unidirectional deletions in pGB2-SS1, the pGB2-SS1 3'-to-5' deletion construct pGB2SS1-CEx2658 was digested with BstWI and SacI.

Serially truncated plasmid DNAs were relegated and were used to transform *E. coli* HB101 bacteria. The deleted plasmids expressed nested series of progressively truncated recombinant proteins that were reacted with human serum antibodies in Western blot assays. Selected plasmids were sequenced to determine the extent of the deletions and to determine the nucleotide coordinates of the deletion clones that defined the boundaries of immunoreactive regions.

Synthesis of fusion proteins, SDS-polyacrylamide gel electrophoresis, and Western blot assays. The expression of recombinant fusion proteins in *E. coli*, sodium dodecyl sulfate (SOS)-polyacrylamide gel electrophoresis, and Western blot assays were performed as described previously (Jenison 1988). In assays to detect the presence of HSV gB-2 antibody reactivities, the bacterial fusion proteins were partially purified from *E. coli* proteins by preparing insoluble protein fractions (Jenison 1988). In epitope mapping studies, whole bacterial lysates were used as antigen targets. Human serum samples were incubated with Western blots at a 1:200 dilution for 16 h at 4° C. Antigen-antibody complexes were detected by incubating the blots with alkaline phosphatase-conjugated goat anti-human IgG antibodies (Southern Biotechnology Associates, Inc.) at a 1:1000 dilution for 4 h at room temperature. Alkaline phosphatase activity was detected by incubating the blots for 10 min in alkaline buffer containing nitroblue tetrazolium and 5-bromo-4-chloro-3-indolyl phosphate.

HSV-2 and HSV-1 antibody reactivities to HSV-2 gB recombinant proteins. Human serum samples were tested for IgG antibody reactivities to the HSV-2 gB recombinant proteins expressed by pGB2-SS2, pGB2-AP2, and pGB2-SS1 (Table 1) in Western blot assays. Amino acid coordinates were numbered by counting the first gB-2 encoded methionine residue as aa 1, and the leucine residue immediately preceding the gB-2 stop codon as aa 904 (this numbering system applies throughout the disclosure). gB-2aa 1 to 22 is a signal sequence that is cleaved during protein maturation. The serum saples had been tested previously for the presence of HSV-1 antibodies and HSV-2 antibodies by using whole viral lysates of HSV-1 and HSV-2 as antigen targets. HSV-1 antibodies and HSV-2 antibodies were defined based upon reactivities to native gG-1 and native gG-2, respectively, in Western blot assays. Serum samples included 23 samples from HSV 1–/2– subjects, 23 samples from HSV 1+/2– subjects, and 18 samples from HSV 1–/2+ subjects.

All serum samples from HSV 1–/2+ subjects reacted strongly with pGB2-SS2 protein and with pGB2-SS1 protein. Eight of 18 HSV1–/2+ subjects also reacted with pGB2-AP2 protein. For HSV 1+/2– subjects, no reactivities to pGB2-SS2 protein or to pGB2-AP2 protein were detected. All HSV 1+/2– subjects reacted with pGB2-SS1 protein. No antibody reactivities to pGB2-SS2, pGB2-AP2, or pGB2-SS1 proteins were detected in the serum samples from HSV 1–/2– subjects. These findings suggested that HSV-2 infections elicit different antibodies that react with amino-proximal and carboxy-proximal segments of gB-2. The data suggested further that HSV-1 infections induce antibodies that cross-react within the carboxy-proximal segment of gB-2, but do not induce antibodies that cross-react within the amino-proximal segment of gB-2. Characteristic results are shown in FIG. 1.

Post immunization Development of anti gB2 human antibodies.

Recombinant proteins expressed by constructs including the HSV-2 type specific epitope (gB2 SS2) and the cross reactive epitope (gB2 SS1) (Table 1) were used as antigen targets in Western immunoblots to evaluate serum antibody reactivities induced by an HSV-2 candidate vaccine compared to the antibody reactivity seen in native HSV-2 infection. Serum samples from 22 individuals known to be HSV-2 seronegative by glycoprotein G (gG) Western blot were evaluated for development of gB2 antibody reactivities post immunization with a recombinant HSV-2 glycoprotein (gB2/gD2/adjuvant) vaccine as described in Burke, *Reviews of Infectious Diseases* 13: 5906–5911 (1991) and Burke, *Microbiol. and Immunol.* 1992, *op.cit.,* incorporated herein by reference. Of 13 HSV 1−/2− vaccinees, all developed gB2 SS2 and SS1 antibody reactivity post-immunization characteristic of those seen in native HSV-2 infection. Of 9 HSV 1+/2− vaccinees, all serum samples were reactive to gB2 SS1 prevaccination and all developed gB2 SS2 antibodies post-immunization. Quantitation of antibody response was performed using serial serum dilutions. A total of 16 post-vaccination serum samples were evaluated, eight each from HSV 1−/2− and HSV 1+/2− vaccinees, and compared to ten serum samples from HSV 2+ individuals. Antibody titers were equivalent between the groups, although HSV 1+/2− vaccinees exhibited a higher range of antibody response than did HSV 1−/2− vaccinees. Median antibody titers were as follows: HSV 1−/2− vaccinees—1:12,800 (range 1:6400 to 1:25,600); for HSV 1+/2− vaccinees—1:25,600 (range 1:12,8000 to 1:25,600, reactivity of two serum samples exceeded maximal dilution); and for HSV 2+ individuals—1:12,800 (range 1:6400 to 1:25, 600). These findings support previous studies using virus neutralization assays indicating that the recombinant gB2/gD2/adjuvant vaccine induces an antibody response equivalent to those seen in native infection. Development of seropositivity to gB2 SS2 is contemplated as a simple assay post-vaccination to assess response.

Localization of a major HSV-2 gB type specific antibody-reactive region. The pGB2-SS2 polypeptide region recognized by HSV-2 antibodies, but not by HSV-1 antibodies, was mapped by using nested sets of serially deleted recombinant proteins. The carboxy terminus boundary was defined by using recombinant proteins that contained carboxy-to-amino terminus deletions. The nucleotide and amino acid coordinates of the deletion constructs are displayed in Tables 1 and 2 below. Thirty-five HSV1−/2+ serum samples were evaluated in order to define the pGB2-SS2 immunoreactive region. The reactivities of three HSV 1−/2+ subjects are shown in FIG. 2. Thirty of 35 serum samples reacted with pGB2SS2-CEx210 protein (amino acids [aa] 18 to 70), and either showed no reactivity or greatly reduced reactivity with pGB2-CEx194 protein (aa 18 to 64). Three of 35 samples reacted with pGB2SS2-CEx219 protein (aa 18 to 75), and had either no or greatly diminished reactivity with pGB2SS2-CEx21O protein (aa 18 to 70). Two of 35 serum samples reacted with pGB2SS2-CEx194 protein (aa 18 to 64) and did not react with the pGB2SS2 CEx163 protein (aa 18 to 54). In summary, the main HSV-2 glycoprotein B type-specific region lay within a segment bounded by amino acids 18 and 75. There were minor differences in the specifics of how HSV-2 antibodies from different subjects reacted with this region. The amino acid sequence of the immunoreactive region is shown in FIGS. 5*a*–5*c*. There is approximately 46% amino acid sequence homology between this region and the corresponding region of HSV-1 gB (FIGS. 4*a*–4*c*).

A minor HSV-2 antibody reactivity, located slightly amino-proximal to the major type-specific reactivity described above, was observed in 12 of 35 HSV 1−/2+ subjects. In each of these 12 serum samples, antibodies reacted with the pGB2SS2-CEx144 protein (aa 18 to 48) but did not react with the pGB2-(aa 18 to 44) protein and more extensively deleted proteins. This minor type specific reactivity therefore was contained within aa 18 to 48.

TABLE 1

Herpesvirus Type 2 Glycoprotein B Expression Constructs

| Construct Name | Nucleotide Coordinates | Amino Acid Coordinates | Expression Vector | Restriction Sites |
|---|---|---|---|---|
| gB2-SS2 | 50-716 | 18-228 | pATH 23 | Sacll-Sacl |
| gB2-AP2 | 407-1511 | 153-503 | pATH 20 | Apol-Pstl |
| gB2-SS1 | 716-2711 | 228-903 | pATH 20 | Sacl-Sacl |
| gB2-HA1 | 50-407 | 18-153 | pATH 23 | Hindlll (pATH 23)-Apol |
| gB2-SMB | 2454-3164 | 819-904 | pATH 10 | Smal-BamH1 |
| gB2-SX0 | 716-1879 | 228-626 | pATH 20 | Sac1-Xhol |
| gB2-SP1 | 716-1511 | 228-503 | pATH 20 | Sac1-Pst1 |

TABLE 2

| | Nucleotide Coordinates | | Amino Acid Coordinates | |
|---|---|---|---|---|
| Construct Name | 5' | 3' | Amino | Carboxy |
| pGB2SS2-CEx83 | 50 | 83 | 18 | 27 |
| pGB2SS2-CEx144 | 50 | 144 | 18 | 48 |
| pGB2SS2-CEx161 | 50 | 161 | 18 | 53 |
| pGB2SS2-CEx163 | 50 | 163 | 18 | 54 |
| pGB2SS2-CEx194 | 50 | 194 | 18 | 64 |
| pGB2SS2-CEx210 | 50 | 210 | 18 | 70 |
| pGB2SS2-CEx219 | 50 | 219 | 18 | 73 |
| pGB2SS2-CEx261 | 50 | 261 | 18 | 87 |
| pGB2SS1-NEx841 | 841 | 2658 | 281 | 856 |
| pGB2SS1-NEx1123 | 1124 | 2658 | 375 | 856 |
| pGB2SS1-NEx1352 | 1352 | 2658 | 452 | 856 |
| pGB2SS1-NEx1642 | 1642 | 2658 | 548 | 856 |
| pGB2SS1-NEx1690 | 1690 | 2658 | 564 | 856 |
| pGB2SS1-NEx1837 | 1837 | 2658 | 613 | 856 |

TABLE 2-continued

| Construct Name | Nucleotide Coordinates | | Amino Acid Coordinates | |
|---|---|---|---|---|
| | 5' | 3' | Amino | Carboxy |
| pGB2SS1-CEx2658 | 683 | 2658 | 229 | 856 |
| pGB2SS1-CEx2029 | 683 | 2029 | 229 | 676 |
| pGB2SS1-CEx1820 | 683 | 1820 | 229 | 606 |
| pGB2SS1-CEx1577 | 683 | 1577 | 229 | 525 |

Localization of a carboxy-proximal gB-2 region recognized by HSV-2 antibodies and by HSV-1 antibodies. All 13 HSV 1+/2− serum samples and 10 of 10 HSV 2+ serum samples tested were reactive to the pGB2-SMB protein (aa 819–904), indicating that the strongest cross-reactive region is contained within the far carboxy-terminus portion of gB-2.

Localization of a second gB-2 region recognized by HSV-2 antibodies and by some HSV-1 cross-reactive antibodies. A second region of pGB2-SS1 protein recognized by HSV-2 antibodies, and by cross-reactive HSV-1 antibodies from some but not all subjects tested, was localized by using nested sets of deleted recombinant proteins. The carboxy terminus boundary of the segment was defined by generating a nested set of carboxy-to-amino terminus deleted recombinant proteins. Serum samples from 21 HSV1−/2+ subjects and 13 HSV 1+/2− subjects were tested. Representative Western blots are shown in FIG. 3. Twenty-one of 21 HSV 1−/2+ serum samples reacted with the gB2-SX0 protein (aa 228 to 626), and showed no reactivity (14 of 21 subjects) or markedly reduced reactivity (7 of 21 subjects) with the pGB2SS1-CEx1820 protein (aa 229 to 606). Six of 13 HSV 1+/2− subjects reacted with the gB2-SX0 (aa 228 to 626), and did not react with the pGB2SS1-CEx1820 protein (aa 229 to 606). These data show that the carboxy terminus boundary of this immunoreactive region lies between aa 606 and 626.

The amino-terminus boundary was determined by using a nested set of amino-to-carboxy deleted proteins. Serum samples from 12 HSV 1+/2− subjects and 15 HSV 1−/2+ subjects were tested. Representative Western blots are shown in FIGS. 3 and 4, Panels B. For all HSV 1+/2− and HSV 1−/2+ serum samples tested, antibodies reacted with pGB2SS1-NEx1690 protein (aa 564 to 856) and did not react with pGB2SS1-NEx1837 protein (aa 613 to 856). Therefore, the amino terminus boundary of this gB2-SS1 immunoreactive region lay between aa 564 and 613.

The mapping of the amino terminus boundary and the carboxy terminus boundary of the immunoreactive region recognized by 21 of 21 HSV 1−/2+ subjects, and by 6 of 13 HSV 1+/2− subjects, localized this reactivity to the gB-2 segment between aa 564 and 626.

Localization of a minor type-specific gB-2 region recognized by some HSV-2 antibodies. A minor type-specific region recognized only by HSV-2 antibodies was detected in 7 of 21 HSV 1−/2+ subjects tested. This segment lies between aa 452 and 503, and it included within the gB-2 coding sequence that is represented both in the carboxy terminus region of pGB2-AP2 and in the amino terminus region of pGB2-SS1. HSV-2 antibodies that react with this minor region encoded by pGB2-SS1 also reacted with the pGB2-AP2 protein.

Localization of a gB-1 segment that reacts with HSV-1 antibodies and that does not react with HSV-2 antibodies. A gB-1 segment from aa 295 to 507 was expressed by the recombinant plasmid pGB1-NSP1. Serum samples from nine HSV 1+/2− reacted strongly with the pGB1-NSP1 protein. Serum samples from eleven HSV 1−/2+ serum samples showed not reactivity with the pGB1-NSP1 protein.

Localization of a second gB-1 segment that reacts with HSV-1 antibodies but not HSV-2 antibodies. This region is bounded by aa 14–110 of HSV gB-1 and is the strongest gB-1 type-specific region. The construct was initially made by a series of cloning steps including aa 42–332 as described above for isolation of gB-2 immunoreactive regions. This region was narrowed using epitope mapping deletion steps which localized the epitope in the far amino terminus region of the protein between aa 14 and 110. PCR was then used to extract small pieces of DNA containing the epitope for cloning into two different expression vectors. The PCR-based region containing the epitope was expressed by the recombinant vectors, and type-specific immunoreactivity against human antibodies was confirmed.

CONCLUSION gB-2 responses induced by HSV-1 infections or by gB-2 immunization include antibodies that cross-react with native gB-1. Similarly, gB-1 responses induced by HSV-1 infections or by gB-1 immunization include antibodies that cross-react with gB-2. However, anti-gB1 antibodies and anti-gB2 antibodies differ in their ability to recognize homologous versus heterologous antigens, and heterologous antibodies are not fully cross-protective in experimental animal models. HSV-1 type-specific immunity has been induced in mice using gB-1 reactive peptides. This observation suggested that gB contains type specific antigenic regions despite the high degree of sequence homology, and that these specific regions might be contained within areas of sequence is not as highly conserved. (*Infect. and Immun.* 31:1062–1070, 1981; *J. Med. Vivol.* 27:309–316, 1989; *J. Virol.* 64:5277–5283, 1990).

Antigenic regions of gB-2 that react with human HSV-2 antibodies and with human HSV-1 antibodies are described. HSV-2 IgG antibodies from all subjects tested reacted with three distinct regions of gB-2: 1) an amino-proximal segment between aa 18 and 75; 2) a carboxy-terminal segment between aa 819 and 904; and 3) a segment between aa 564 and 626. HSV-1 antibodies also reacted within the latter two segments, but did not react with the amino-proximal segment.

The amino-proximal segment (aa 18 to 75) reacted strongly with all HSV 1−/2+ samples and did not react with HSV 1+/2− samples. This region is one of the most divergent between gB-1 and gB-2, with an amino acid sequence homology of 46% (compared to an overall gB amino acid sequence homology of 86%). The biologic properties of this region remain to be defined, although it includes the predicted extracytoplasmic domain of gB (*J. Viral.* 61: 326–335, 1987; *Virol* 155:322–333, 1986; *J. Mol. Biol.* 201:575–588, 1988).

A second gB-2 region recognized by all HSV 1−/2+ subjects was localized to a carboxy-terminal segment between aa 819 and 904. This region was recognized also by antibodies from all HSV 1+/2− subjects. Therefore, this region contains a major epitope(s) recognized by HSV-2 antibodies and also contains the dominant cross-reactive epitope(s) recognized by HSV-1 antibodies. This segment is within an area of high amino acid sequence homology that lies carboxy-proximal to the membrane spanning domain of gB and includes a 39 aa region thought to be essential for membrane fusion. The corresponding region in gB-1 is thought to be cytoplasmic, as may be predicted in nonspecific but conserved protein domains.

The third immunoreactive region recognized by HSV-2 antibodies lies within the segment between aa 564 and 626, amino-proximal to the proposed membrane spanning domain. This segment reacted with antibodies from all HSV-2 seropositive subjects tested, and cross-reacted with antibodies with some but not all HSV-1 seropositive subjects tested.

No HSV-2 antibody reactivities or HSV-1 antibody reactivities were detected in the gB-2 region between aa 70 and 452. This region includes a segment between aa 108 and 395 that is extremely highly conserved between gB-1 and gB-2 (98% homology). A strongly reactive HSV-1 antibody type-specific region was identified between amino acids 14 to 110. This polypeptide segment also reacted with HSV-1 antibodies, but not HSV-2 antibodies.

An HSV-1 type-specific region was identified between gB-1 amino acids 295 and 507. This gB-1 polypeptide segment reacted with HSV-1 antibodies but did not react with HSV-2 antibodies.

Human antibody responses following acute HSV infections are complex, with appearance of sequential glycoprotein antibody reactivities beginning at approximately 4 days following infection. In HSV-2 infections, gB-2 and then gD-2 antibodies appear first. Seroconversion to all antigenic determinants requires at least 21 days post infection in most cases (*J. Med. Virol.* 17:153–166, 1985). Extensive cross-reactivity occurs between HSV-1 and HSV-2 proteins, and between HSV-2 antibodies and HSV-1 proteins (*Am. J. Eni.* 104:192–201, 1976). Virus type specific reactivities have been described previously for gG-1 and gG-2, and for the HSV-1 glycoprotein C. Detection of HSV-2 type specific reactivities to gG-2 by using an immunodot assay was one of the earliest indication that an HSV surface glycoprotein elicited type specific reactivities (*J. Clin. Micro.* 22:641–644, 1985). Western blot assays using viral lysates of HSV-1 and HSV-2 as antigen targets can detect type specific human antibody responses to several proteins including gG. Such assays have been invaluable tools in HSV clinical diagnosis and in HSV seroepidemiology studies. gG-based type specific seroassays, while sensitive and specific, are currently limited in availability due to difficulty in preparation of reagents and the need for expertise in interpretation of results. Potential limitations to gG-2 testing include the time interval between infection and the appearance of serum gG antibodies (which may require up to 8 weeks), and the lack of detectable anti-gG antibodies in approximately 5% of infected subjects (*Genitourin. Med.* 69:174–183, 1993). Use of type-specific gB-1 and gB-2 recombinant proteins as reagents in serodiagnostic assays may therefore complement existing gG-based assays.

SEQUENCE LISTING (1) GENERAL INFORMATION:

(iii) NUMBER OF SEQUENCES:2

(2) INFORMATION FOR SEQ ID NO: 1:

(i) SEQUENCE CHARACTERISTICS:
      (A) LENGTH: 904 amino acids
      (B) TYPE: amino acid
      (D) TOPOLOGY: linear (x) PUBLICATION INFORMATION:
      (K) RELEVANT RESIDUES IN SEQ ID NO:1: FROM 14-110; 295-507;
         814-901

(xi) SEQUENCE DESCRIPTION: SEQ ID NO:1:

```
Met Arg Gln Gly Ala Pro Ala Arg Gly Arg Arg Trp Phe Val Val Trp
                 5                  10                  15

Ala Leu Leu Gly Leu Thr Leu Gly Val Leu Val Ala Ser Ala Ala Pro
             20                  25                  30

Ser Ser Pro Gly Thr Pro Gly Val Ala Ala Ala Thr Gln Ala Ala Asn
         35                  40                  45

Gly Gly Pro Ala Thr Pro Ala Pro Pro Ala Pro Gly Ala Pro Pro Thr
 50                  55                  60

Gly Asp Pro Lys Pro Lys Lys Asn Arg Lys Pro Lys Pro Pro Lys Pro
 65                  70                  75                  80

Pro Arg Pro Ala Gly Asp Asn Ala Thr Val Ala Ala Gly His Ala Thr
             85                  90                  95

Leu Arg Glu His Leu Arg Asp Ile Lys Ala Glu Asn Thr Asp Ala Asn
            100                 105                 110

Phe Tyr Val Cys Pro Pro Pro Thr Gly Ala Thr Val Val Gln Phe Glu
            115                 120                 125
```

```
Gln Pro Arg Arg Cys Pro Thr Arg Pro Glu Gly Gln Asn Tyr Thr Glu
    130                 135                 140
Gly Ile Ala Val Val Phe Lys Glu Asn Ile Ala Pro Tyr Lys Phe Lys
145                 150                 155                 160
Ala Thr Met Tyr Tyr Lys Asp Val Thr Val Ser Gln Val Trp Phe Gly
                165                 170                 175
His Arg Tyr Ser Gln Phe Met Gly Ile Phe Glu Asp Arg Ala Pro Val
            180                 185                 190
Pro Phe Glu Glu Val Ile Asp Lys Ile Asn Ala Lys Gly Val Cys Arg
        195                 200                 205
Ser Thr Ala Lys Tyr Val Arg Asn Asn Leu Glu Thr Thr Ala Phe His
    210                 215                 220
Arg Asp Asp His Glu Thr Asp Met Glu Leu Lys Pro Ala Asn Ala Ala
225                 230                 235                 240
Thr Arg Thr Ser Arg Gly Trp His Thr Thr Asp Leu Lys Tyr Asn Pro
                245                 250                 255
Ser Arg Val Glu Ala Phe His Arg Tyr Gly Thr Thr Val Asn Cys Ile
            260                 265                 270
Val Glu Glu Val Asp Ala Arg Ser Val Tyr Pro Tyr Asp Glu Phe Val
        275                 280                 285
Leu Ala Thr Gly Asp Phe Val Tyr Met Ser Pro Phe Tyr Gly Tyr Arg
    290                 295                 300
Glu Gly Ser His Thr Glu His Thr Ser Tyr Ala Ala Asp Arg Phe Lys
305                 310                 315                 320
Gln Val Asp Gly Phe Tyr Ala Arg Asp Leu Thr Thr Lys Ala Arg Ala
                325                 330                 335
Thr Ala Pro Thr Thr Arg Asn Leu Leu Thr Thr Pro Lys Phe Thr Val
            340                 345                 350
Ala Trp Asp Trp Val Pro Lys Arg Pro Ser Val Cys Thr Met Thr Lys
        355                 360                 365
Trp Gln Glu Val Asp Glu Met Leu Arg Ser Glu Tyr Gly Gly Ser Phe
    370                 375                 380
Arg Phe Ser Ser Asp Ala Ile Ser Thr Thr Phe Thr Thr Asn Leu Thr
385                 390                 395                 400
Glu Tyr Pro Leu Ser Arg Val Asp Leu Gly Asp Cys Ile Gly Lys Asp
                405                 410                 415
Ala Arg Asp Ala Met Asp Arg Ile Phe Ala Arg Tyr Asn Ala Thr
            420                 425                 430
His Ile Lys Val Gly Gln Pro Gln Tyr Tyr Leu Ala Asn Gly Gly Phe
        435                 440                 445
Leu Ile Ala Tyr Gln Pro Leu Leu Ser Asn Thr Leu Ala Glu Leu Tyr
    450                 455                 460
Val Arg Glu His Leu Arg Glu Gln Ser Arg Lys Pro Pro Asn Pro Thr
465                 470                 475                 480
Pro Pro Pro Pro Gly Ala Ser Ala Asn Ala Ser Val Glu Arg Ile Lys
                485                 490                 495
Thr Thr Ser Ser Ile Glu Phe Ala Arg Leu Gln Phe Thr Tyr Asn His
            500                 505                 510
Ile Gln Arg His Val Asn Asp Met Leu Gly Arg Val Ala Ile Ala Trp
        515                 520                 525
Cys Glu Leu Gln Asn His Glu Leu Thr Leu Trp Asn Glu Ala Arg Lys
    530                 535                 540
```

```
Leu Asn Pro Asn Ala Ile Ala Ser Ala Thr Val Gly Arg Arg Val Ser
545                 550                 555                 560

Ala Arg Met Leu Gly Asp Val Met Ala Val Ser Thr Cys Val Pro Val
                565                 570                 575

Ala Ala Asp Asn Val Ile Val Gln Asn Ser Met Arg Ile Ser Ser Arg
            580                 585                 590

Pro Gly Ala Cys Tyr Ser Arg Pro Leu Val Ser Phe Arg Tyr Glu Asp
        595                 600                 605

Gln Gly Pro Leu Val Glu Gly Gln Leu Gly Glu Asn Asn Glu Leu Arg
610                 615                 620

Leu Thr Arg Asp Ala Ile Glu Pro Cys Thr Val Gly His Arg Arg Tyr
625                 630                 635                 640

Phe Thr Phe Gly Gly Gly Tyr Val Tyr Phe Glu Glu Tyr Ala Tyr Ser
                645                 650                 655

His Gln Leu Ser Arg Ala Asp Ile Thr Thr Val Ser Thr Phe Ile Asp
            660                 665                 670

Leu Asn Ile Thr Met Leu Glu Asp His Glu Phe Val Pro Leu Glu Val
        675                 680                 685

Tyr Thr Arg His Glu Ile Lys Asp Ser Gly Leu Leu Asp Tyr Thr Glu
690                 695                 700

Val Gln Arg Arg Asn Gln Leu His Asp Leu Arg Phe Ala Asp Ile Asp
705                 710                 715                 720

Thr Val Ile His Ala Asp Ala Asn Ala Ala Met Phe Ala Gly Leu Gly
                725                 730                 735

Ala Phe Phe Glu Gly Met Gly Asp Leu Gly Arg Ala Val Gly Lys Val
            740                 745                 750

Val Met Gly Ile Val Gly Gly Val Ser Ala Val Ser Gly Val Ser
        755                 760                 765

Ser Phe Met Ser Asn Pro Phe Gly Ala Leu Ala Val Gly Leu Leu Val
770                 775                 780

Leu Ala Gly Leu Ala Ala Ala Phe Phe Ala Phe Arg Tyr Val Met Arg
785                 790                 795                 800

Leu Gln Ser Asn Pro Met Lys Ala Leu Tyr Pro Leu Thr Thr Lys Glu
                805                 810                 815

Leu Lys Asn Pro Thr Asn Pro Asp Ala Ser Gly Glu Gly Glu Glu Gly
            820                 825                 830

Gly Asp Phe Asp Glu Ala Lys Leu Ala Glu Ala Arg Glu Met Ile Arg
        835                 840                 845

Tyr Met Ala Leu Val Ser Ala Met Glu Arg Thr Glu His Lys Ala Lys
850                 855                 860

Lys Lys Gly Thr Ser Ala Leu Leu Ser Ala Lys Val Thr Asp Met Val
865                 870                 875                 880

Met Arg Lys Arg Arg Asn Thr Asn Tyr Thr Gln Val Pro Asn Lys Asp
                885                 890                 895

Gly Asp Ala Asp Glu Asp Leu
            900         904

(2) INFORMATION FOR SEQ ID NO: 2:

(i) SEQUENCE CHARACTERISTICS:
        (A) LENGTH: 904 amino acids
        (B) TYPE: amino acid
        (D) TOPOLOGY: linear (x) PUBLICATION INFORMATION:
        (K) RELEVANT RESIDUES IN SEQ ID NO:2: FROM 18-75; 819-904
```

(xi) SEQUENCE DESCRIPTION: SEQ ID NO:2:

```
Met Arg Gly Gly Gly Leu Ile Cys Ala Leu Val Val Gly Ala Leu Val
 1               5                  10                  15

Ala Ala Val Ala Ser Ala Ala Pro Ala Ala Pro Ala Ala Pro Arg Ala
             20                  25                  30

Ser Gly Gly Val Ala Ala Thr Val Ala Ala Asn Gly Gly Pro Ala Ser
         35                  40                  45

Arg Pro Pro Pro Val Pro Ser Pro Ala Thr Thr Lys Ala Arg Lys Arg
     50                  55                  60

Lys Thr Lys Lys Pro Pro Lys Arg Pro Glu Ala Thr Pro Pro Pro Asp
 65                  70                  75                  80

Ala Asn Ala Thr Val Ala Ala Gly His Ala Thr Leu Arg Ala His Leu
                 85                  90                  95

Arg Glu Ile Lys Val Glu Asn Ala Asp Ala Gln Phe Tyr Val Cys Pro
            100                 105                 110

Pro Pro Thr Gly Ala Thr Val Val Gln Phe Glu Gln Pro Arg Arg Cys
        115                 120                 125

Pro Thr Arg Pro Glu Gly Gln Asn Tyr Thr Glu Gly Ile Ala Val Val
    130                 135                 140

Phe Lys Glu Asn Ile Ala Pro Tyr Lys Phe Lys Ala Thr Met Tyr Tyr
145                 150                 155                 160

Lys Asp Val Thr Val Ser Gln Val Trp Phe Gly His Arg Tyr Ser Gln
                165                 170                 175

Phe Met Gly Ile Phe Glu Asp Arg Ala Pro Val Pro Phe Glu Glu Val
            180                 185                 190

Ile Asp Lys Ile Asn Ala Lys Gly Val Cys Arg Ser Thr Ala Lys Tyr
        195                 200                 205

Val Arg Asn Asn Met Glu Thr Thr Ala Phe His Arg Asp Asp His Glu
    210                 215                 220

Thr Asp Met Glu Leu Lys Pro Ala Lys Val Ala Thr Arg Thr Ser Arg
225                 230                 235                 240

Gly Trp His Thr Thr Asp Leu Lys Tyr Asn Pro Ser Arg Val Glu Ala
                245                 250                 255

Phe His Arg Tyr Gly Thr Thr Val Asn Cys Ile Val Glu Glu Val Asp
            260                 265                 270

Ala Arg Ser Val Tyr Pro Tyr Asp Glu Phe Val Leu Ala Thr Gly Asp
        275                 280                 285

Phe Val Tyr Met Ser Pro Phe Tyr Gly Tyr Arg Glu Gly Ser His Thr
    290                 295                 300

Glu His Thr Ser Tyr Ala Ala Asp Arg Phe Lys Gln Val Asp Gly Phe
305                 310                 315                 320

Tyr Ala Arg Asp Leu Thr Thr Lys Ala Arg Ala Thr Ser Pro Thr Thr
                325                 330                 335

Arg Asn Leu Leu Thr Thr Pro Lys Phe Thr Val Ala Trp Asp Trp Val
            340                 345                 350

Pro Lys Arg Pro Ala Val Cys Thr Met Thr Lys Trp Gln Glu Val Asp
        355                 360                 365

Glu Met Leu Arg Ala Glu Tyr Gly Gly Ser Phe Arg Phe Ser Ser Asp
    370                 375                 380

Ala Ile Ser Thr Thr Phe Thr Thr Asn Leu Thr Gln Tyr Ser Leu Ser
385                 390                 395                 400

Arg Val Asp Leu Gly Asp Cys Ile Gly Arg Asp Ala Arg Glu Ala Ile
```

-continued

```
                405                 410                 415
Asp Arg Met Phe Ala Arg Lys Tyr Asn Ala Thr His Ile Lys Val Gly
                420                 425                 430
Gln Pro Gln Tyr Tyr Leu Ala Thr Gly Gly Phe Leu Ile Ala Tyr Gln
                435                 440                 445
Pro Leu Leu Ser Asn Thr Leu Ala Glu Leu Tyr Val Arg Glu Tyr Met
450                 455                 460
Arg Glu Gln Asp Arg Lys Pro Arg Asn Ala Thr Pro Ala Pro Leu Arg
465                 470                 475                 480
Glu Ala Pro Ser Ala Asn Ala Ser Val Glu Arg Ile Lys Thr Thr Ser
                485                 490                 495
Ser Ile Glu Phe Ala Arg Leu Gln Phe Thr Tyr Asn His Ile Gln Arg
                500                 505                 510
His Val Asn Asp Met Leu Gly Arg Ile Ala Val Ala Trp Cys Glu Leu
                515                 520                 525
Gln Asn His Glu Leu Thr Leu Trp Asn Glu Ala Arg Lys Leu Asn Pro
                530                 535                 540
Asn Ala Ile Ala Ser Ala Thr Val Gly Arg Arg Val Ser Ala Arg Met
545                 550                 555                 560
Leu Gly Asp Val Met Ala Val Ser Thr Cys Val Pro Val Ala Pro Asp
                565                 570                 575
Asn Val Ile Val Gln Asn Ser Met Arg Val Ser Ser Arg Pro Gly Thr
                580                 585                 590
Cys Tyr Ser Arg Pro Leu Val Ser Phe Arg Tyr Glu Asp Gln Gly Pro
                595                 600                 605
Leu Ile Glu Gly Gln Leu Gly Glu Asn Asn Glu Leu Arg Leu Thr Arg
                610                 615                 620
Asp Ala Leu Glu Pro Cys Thr Val Gly His Arg Arg Tyr Phe Ile Phe
625                 630                 635                 640
Gly Gly Gly Tyr Val Tyr Phe Glu Glu Tyr Ala Tyr Ser His Gln Leu
                645                 650                 655
Ser Arg Ala Asp Val Thr Thr Val Ser Thr Phe Ile Asp Leu Asn Ile
                660                 665                 670
Thr Met Leu Glu Asp His Glu Phe Val Pro Leu Glu Val Tyr Thr Arg
                675                 680                 685
His Glu Ile Lys Asp Ser Gly Leu Leu Asp Tyr Thr Glu Val Gln Arg
                690                 695                 700
Arg Asn Gln Leu His Asp Leu Arg Phe Ala Asp Ile Asp Thr Val Ile
705                 710                 715                 720
Arg Ala Asp Ala Asn Ala Ala Met Phe Ala Gly Leu Cys Ala Phe Phe
                725                 730                 735
Glu Gly Met Gly Asp Leu Gly Arg Ala Val Gly Lys Val Val Met Gly
                740                 745                 750
Val Val Gly Gly Val Val Ser Ala Val Ser Gly Val Ser Ser Phe Met
                755                 760                 765
Ser Asn Pro Phe Gly Ala Leu Ala Val Gly Leu Leu Val Leu Ala Gly
                770                 775                 780
Leu Val Ala Ala Phe Phe Ala Phe Arg Tyr Val Leu Gln Leu Gln Arg
785                 790                 795                 800
Asn Pro Met Lys Ala Leu Tyr Pro Leu Thr Thr Lys Glu Leu Lys Thr
                805                 810                 815
Ser Asp Pro Gly Gly Val Gly Gly Glu Gly Glu Glu Gly Ala Glu Gly
                820                 825                 830
```

―continued

```
Gly Gly Phe Asp Glu Ala Lys Leu Ala Glu Ala Arg Glu Met Ile Arg
        835             840             845

Tyr Met Ala Leu Val Ser Ala Met Glu Arg Thr Glu His Lys Ala Arg
    850             855             860

Lys Lys Gly Thr Ser Ala Leu Leu Ser Ser Lys Val Thr Asn Met Val
865             870             875                     880

Leu Arg Lys Arg Asn Lys Ala Arg Tyr Ser Pro Leu His Asn Glu Asp
                885             890             895

Glu Ala Gly Asp Glu Asp Glu Leu
            900         904
```

What is claimed is:

1. A continuous, isolated, antigenic polypeptide segment of herpes simplex virus (HSV) glycoprotein B2 (gB2) according to sequence ID number 2 which is reactive with human antibodies to HSV-2 infection, wherein the antigenic segment is selected from the group consisting of a) continuous HSV gB2 type-specific polypeptide segments which are isolated from cross-reactive epitopes and which contain a type-specific epitope subtended by amino acids 18–75; b) continuous HSV gB2 cross-reactive polypeptide segments, subtended by amino acids 564–626; and c) continuous HSV gB2 cross-reactive polypeptide segments subtended by amino acids 819–904.

2. A type-specific antigenic polypeptide segment of herpes simplex virus (HSV) glycoprotein B2 (gB2) according to claim 1.

3. An immunoassay for distinguishing an HSV-1 infection from an HSV-2 infection in a human, comprising contacting a blood sample of the human for antibodies immunoreactive with the type-specific antigenic polypeptide segment of claim 2 detecting antigen/antibody complex.

4. A cross-reactive antigenic polypeptide segment of herpes simplex virus (HSV) glycoprotein B2 (gB2) according to claim 1.

5. A cross-reactive antigenic polypeptide segment according to claim 4, subtended by amino acids 819–904 of HSV gB2.

6. A cross-reactive antigenic polypeptide segment according to claim 4, subtended by amino acids 564 and 626 of HSV gB2.

7. An immunoassay for diagnosing an HSV-1 infection or an HSV-2 infection in a human, comprising contacting a blood sample of the human for antibodies immunoreactive with a cross-reactive antigenic polypeptide segment according to claim 1 and detecting antigen/antibody complex.

8. A continuous, isolated, antigenic polypeptide segment of herpes simplex virus (HSV) glycoprotein B1 (gB1) according to sequence ID number 1 which is reactive with human antibodies to HSV-1 infection, wherein the antigenic polypeptide segment is selected from the group consisting of a) a type-specific antigenic polypeptide segment subtended by amino acids 14–110; b) a type-specific antigenic polypeptide segment subtended by amino acids 295–507; and c) a cross-reactive antigenic polypeptide segment subtended by amino acids 814–901.

9. A dominant type-specific antigenic polypeptide segment according to claim 8, subtended by amino acids 14–110 of HSV gB1.

10. An immunoassay for distinguishing an HSV-1 infection from an HSV-2 infection in a human, comprising contacting a blood sample of the human for antibodies immunoreactive with the type-specific antigenic polypeptide segment of claim 9 and detecting antigen/antibody complex.

11. A type-specific antigenic polypeptide segment according to claim 8, subtended by amino acids 295–507 of HSV gB1.

12. An immunoassay for distinguishing an HSV-1 infection from an HSV-2 infection in a human, comprising contacting a blood sample of the human for antibodies immunoreactive with the type-specific antigenic polypeptide segment of claim 11 and detecting antigen/antibody complex.

13. A cross-reactive antigenic polypeptide segment of herpes simplex virus (HSV) glycoprotein gB1 according to claim 8, subtended by amino acids 814–901 of HSV gB1.

14. An immunoassay for diagnosing an HSV-1 infection or an HSV-2 infection in a human, comprising contacting a blood sample of the human for antibodies immunoreactive with a cross-reactive antigenic polypeptide segment according to claim 8 and detecting antigen/antibody complex.

15. A continuous isolated, antigenic polypeptide segment of herpes simplex virus (HSV) glycoprotein B2 (gB2) according to sequence ID number 2 which is reactive with human antibodies to HSV-2 infection, wherein the antigenic segment comprises continuous HSV gB2 type-specific polypeptide segments which are cross-reactive epitopes and which contain a type-specific epitope subtended by amino acids 18–75.

16. An immunoassay for distinguishing an HSV-1 infection from an HSV-2 infection in a human, comprising contacting a blood sample of the human for antibodies immunoreactive with the type-specific antigenic polypeptide segment of claim 15, and detecting antigen/antibody complex.

* * * * *